(12) United States Patent
Taylor, Jr. et al.

(10) Patent No.: US 6,419,630 B1
(45) Date of Patent: Jul. 16, 2002

(54) VITAL SIGNS MONITORING SYSTEM

(76) Inventors: Stanley A. Taylor, Jr.; Marcella T. Taylor, both of 2504 Charter Oak Dr., Waldorf, MD (US) 20601

( * ) Notice: Subject to any disclaimer, the term of this patent is extended or adjusted under 35 U.S.C. 154(b) by 0 days.

(21) Appl. No.: 09/797,658

(22) Filed: Mar. 5, 2001

(51) Int. Cl.[7] ............................... A61B 5/00; G04F 1/00
(52) U.S. Cl. ..................... 600/301; 600/549; 128/903; 128/920; 348/734; 348/77; 368/28; 368/10; 340/309.15; 702/177
(58) Field of Search ................ 600/300–301, 600/481–486, 500–503, 508, 549; 128/903, 904, 920, 925, 897–898; 434/307 R, 262, 236, 238, 237; 345/501–506, 519–520, 522; 348/725, 734, 77, 844; 368/28, 10, 62, 72–73, 327; 340/309.15–309.6; 702/177–178; 482/7–8, 9, 901–902

(56) References Cited

U.S. PATENT DOCUMENTS

| | | | | |
|---|---|---|---|---|
| 4,051,522 A | * | 9/1977 | Healy et al. | ................. 128/903 |
| 4,278,095 A | | 7/1981 | Lapeyre | |
| 4,807,639 A | | 2/1989 | Shimizu et al. | |
| 5,088,056 A | * | 2/1992 | McIntosh et al. | ........... 702/177 |
| 5,099,463 A | * | 3/1992 | Lloyd et al. | ................... 368/10 |
| 5,412,419 A | * | 5/1995 | Ziarati | ......................... 348/61 |
| 5,527,239 A | * | 6/1996 | Abbondanza | .................. 482/8 |
| 5,601,435 A | | 2/1997 | Quy | |
| 5,672,107 A | | 9/1997 | Clayman | |
| D387,352 S | | 12/1997 | Kaneko et al. | |
| 5,776,056 A | * | 7/1998 | Bu et al. | ..................... 600/301 |
| 6,163,281 A | * | 12/2000 | Torch | .......................... 341/21 |
| 6,233,539 B1 | * | 5/2001 | Brown | ........................ 600/300 |
| 6,249,809 B1 | * | 6/2001 | Bro | ............................. 709/217 |

* cited by examiner

*Primary Examiner*—Kevin Shaver
*Assistant Examiner*—Michael C Astorino

(57) ABSTRACT

A vital signs monitoring system for allowing a user to easily monitor their vital signs at home with a remote control type device. The vital signs monitoring system includes a remote control for a television that has a plurality of sensors designed for monitoring the vital signs of a user. A first transceiver is positioned in the housing such that the transceiver is operationally coupled to the sensors whereby the first transceiver is for transmitting vital sign information collected by the sensors. A television has a second transceiver for receiving the information collected by the sensors, the television has a processing unit operationally coupled to the second transceiver such that the processing unit processes information received by the second transceiver. The television is for displaying the information on a screen of the television.

10 Claims, 3 Drawing Sheets

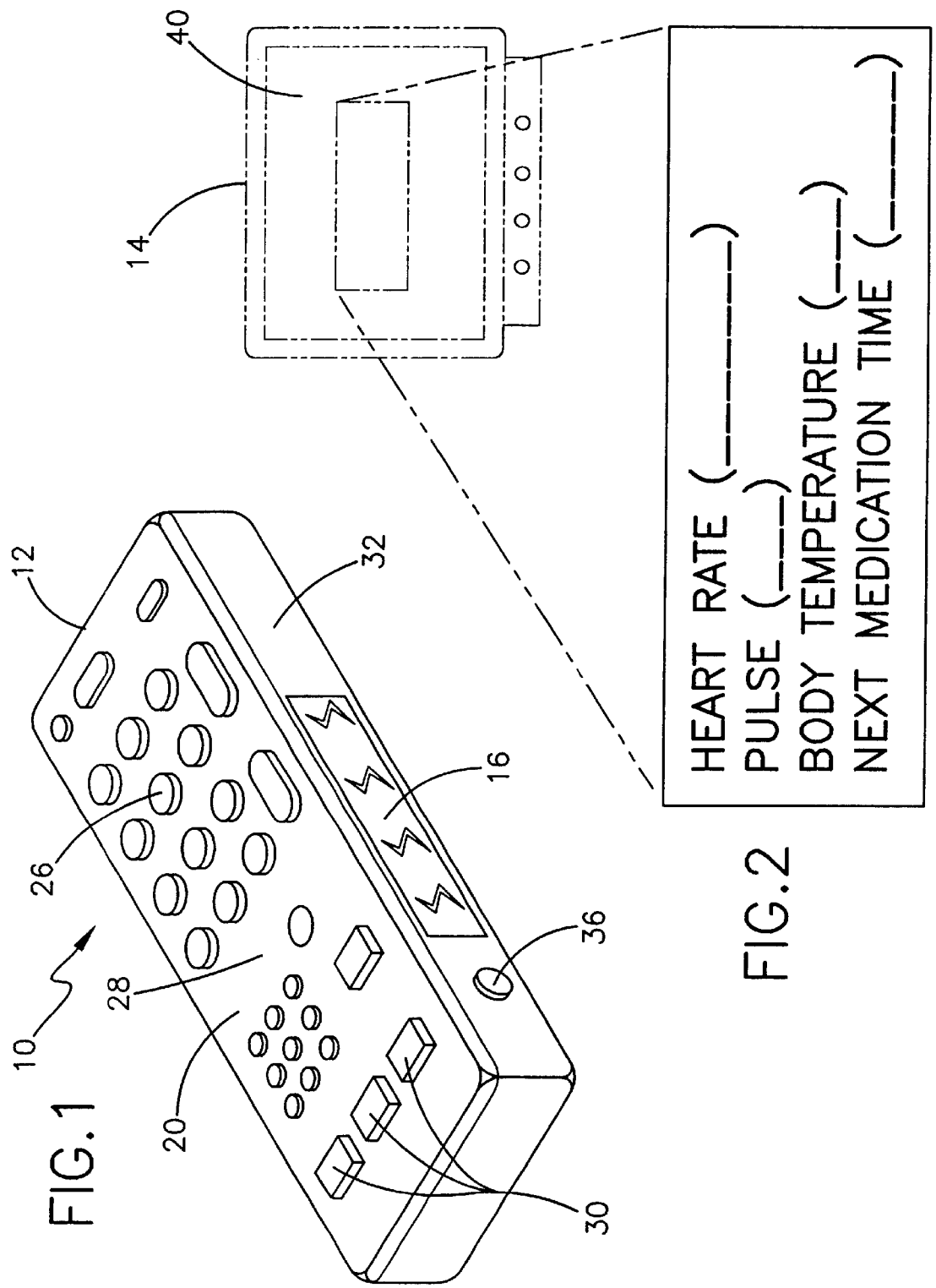

VITAL SIGNS MONITORING SYSTEM

BACKGROUND OF THE INVENTION

1. Field of the Invention

The present invention relates to vital sign monitoring systems and more particularly pertains to a new vital signs monitoring system for allowing a user to easily monitor their vital signs at home with a remote control type device.

2. Description of the Prior Art

The use of vital sign monitoring systems is known in the prior art. More specifically, vital sign monitoring systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,278,095; U.S. Pat. No. 5,601,435; U.S. Pat. No. 5,776,056; U.S. Pat. No. 5,672,107; U.S. Pat. No. 4,807,639; and U.S. Pat. No. Des. 387,352.

While these devices fulfill their respective, particular objectives and requirements, the aforementioned patents do not disclose a new vital signs monitoring system. The inventive device includes a remote control for a television that has a plurality of sensors designed for monitoring the vital signs of a user. A first transceiver is positioned in the housing such that the transceiver is operationally coupled to the sensors whereby the first transceiver is for transmitting vital sign information collected by the sensors. A television has a second transceiver for receiving the information collected by the sensors, the television has a processing unit operationally coupled to the second transceiver such that the processing unit processes information received by the second transceiver. The television is for displaying the information on a screen of the television.

In these respects, the vital signs monitoring system according to the present invention substantially departs from the conventional concepts and designs of the prior art, and in so doing provides an apparatus primarily developed for the purpose of allowing a user to easily monitor their vital signs at home with a remote control type device.

SUMMARY OF THE INVENTION

In view of the foregoing disadvantages inherent in the known types of vital sign monitoring systems now present in the prior art, the present invention provides a new vital signs monitoring system construction wherein the same can be utilized for allowing a user to easily monitor their vital signs at home with a remote control type device.

The general purpose of the present invention, which will be described subsequently in greater detail, is to provide a new vital signs monitoring system apparatus and method which has many of the advantages of the vital sign monitoring systems mentioned heretofore and many novel features that result in a new vital signs monitoring system which is not anticipated, rendered obvious, suggested, or even implied by any of the prior art vital sign monitoring systems, either alone or in any combination thereof.

To attain this, the present invention generally comprises a remote control for a television that has a plurality of sensors designed for monitoring the vital signs of a user. A first transceiver is positioned in the housing such that the transceiver is operationally coupled to the sensors whereby the first transceiver is for transmitting vital sign information collected by the sensors. A television has a second transceiver for receiving the information collected by the sensors, the television has a processing unit operationally coupled to the second transceiver such that the processing unit processes information received by the second transceiver. The television is for displaying the information on a screen of the television.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new vital signs monitoring system apparatus and method which has any of the advantages of the vital sign monitoring systems mentioned heretofore and many novel features that result in a new vital signs monitoring system which is not anticipated, rendered obvious, suggested, or even implied by any of the prior art vital sign monitoring systems, either alone or in any combination thereof.

It is another object of the present invention to provide a new vital signs monitoring system which may be easily and efficiently manufactured and marketed.

It is a further object of the present invention to provide a new vital signs monitoring system which is of a durable and reliable construction.

An even further object of the present invention is to provide a new vital signs monitoring system which is susceptible of a low cost of manufacture with regard to both materials and labor, and which accordingly is then susceptible of low prices of sale to the consuming public, thereby making such vital signs monitoring system economically available to the buying public.

Still yet another object of the present invention is to provide a new vital signs monitoring system which provides in the apparatuses and methods of the prior art some of the advantages thereof, while simultaneously overcoming some of the disadvantages normally associated therewith.

Still another object of the present invention is to provide a new vital signs monitoring system for allowing a user to easily monitor their vital signs at home with a remote control type device.

Yet another object of the present invention is to provide a new vital signs monitoring system which includes a remote control for a television that has a plurality of sensors designed for monitoring the vital signs of a user. A first transceiver is positioned in the housing such that the transceiver is operationally coupled to the sensors whereby the first transceiver is for transmitting vital sign information collected by the sensors. A television has a second transceiver for receiving the information collected by the sensors, the television has a processing unit operationally coupled to the second transceiver such that the processing unit processes information received by the second transceiver. The television is for displaying the information on a screen of the television.

Still yet another object of the present invention is to provide a new vital signs monitoring system that allow a user to easily track their vital signs and set programmable reminders and display features for medications and times would help the user to take all his or her medication on time, while the help button would trigger an autodialing message machine to summon emergency assistance.

Even still another object of the present invention is to provide a new vital signs monitoring system that would integrate with a users current television and be user friendly.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new vital signs monitoring system according to the present invention.

FIG. 2 is a perspective view of the present invention.

DESCRIPTION OF THE PREFERRED EMBODIMENT

Figure 3:
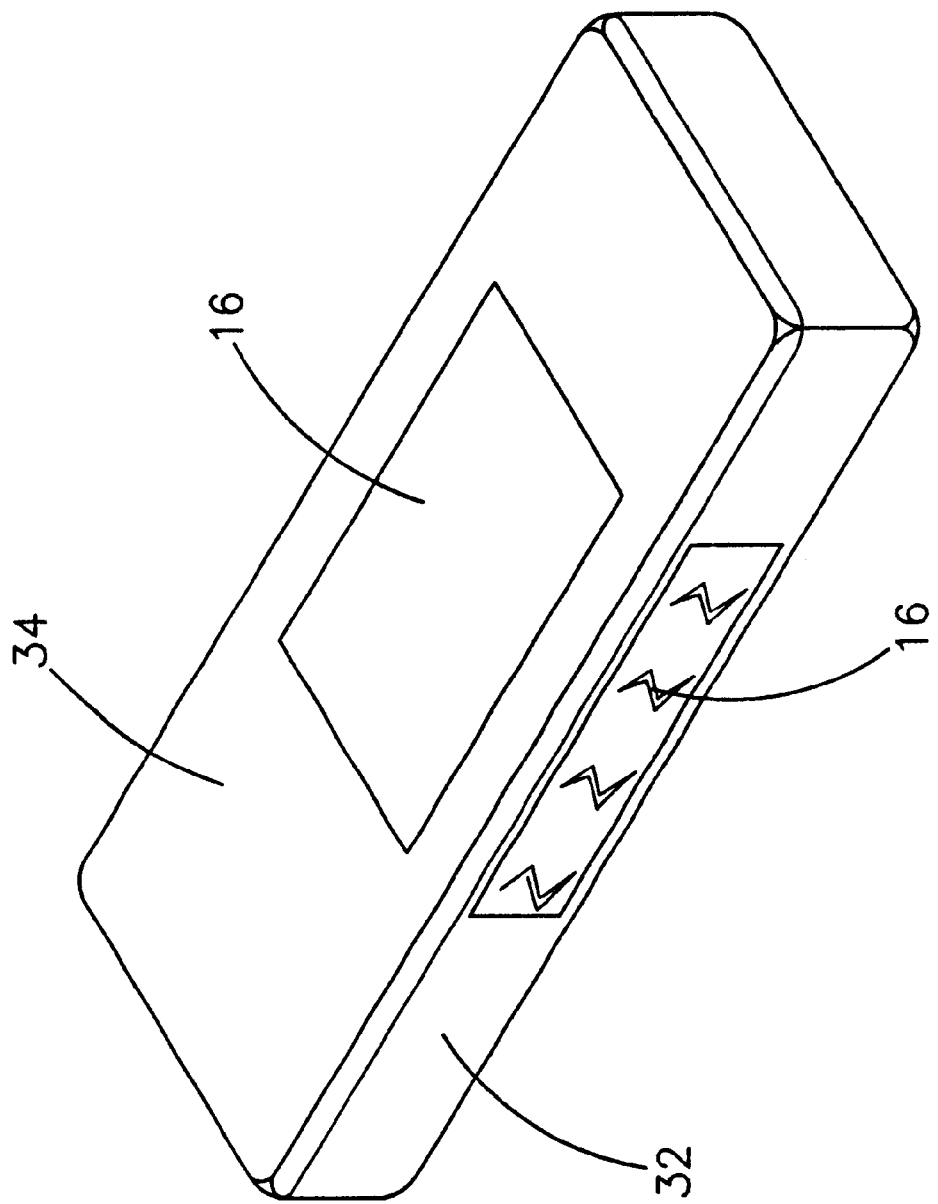
FIG. 3 is a bottom view of the present invention.
Figure 4:
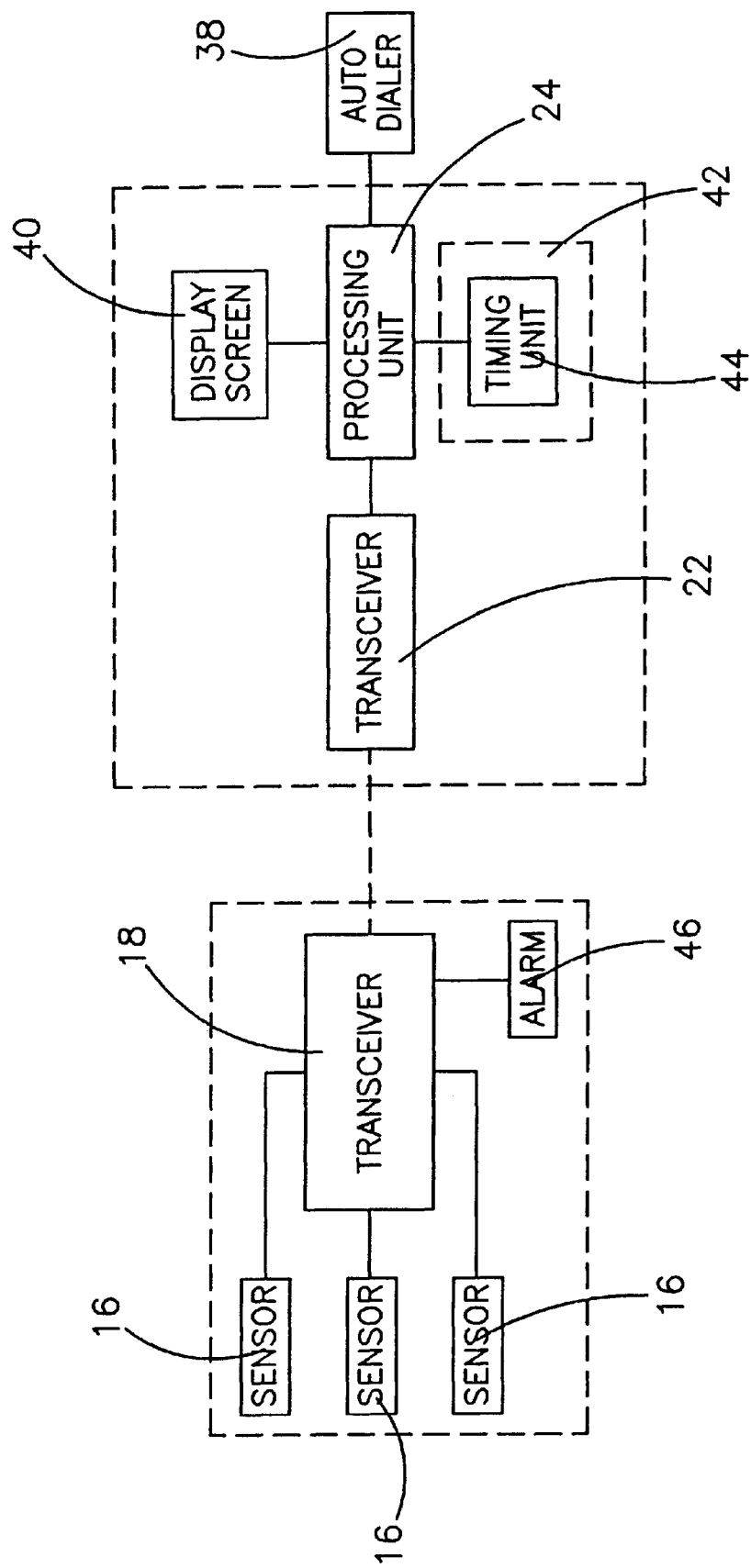
FIG. 4 is a block diagram of the present invention.

With reference now to the drawings, and in particular to FIGS. 1 through 4 thereof, a new vital signs monitoring system embodying the principles and concepts of the present invention and generally designated by the reference numeral 10 will be described.

As best illustrated in FIGS. 1 through 4, the vital signs monitoring system 10 generally comprises a remote control 12 for a television 14 that has a plurality of sensors 16 designed for monitoring the vital signs of a user. A first transceiver 18 is positioned in the housing 20 such that the transceiver 18 is operationally coupled to the sensors 16 whereby the first transceiver 18 is for transmitting vital sign information collected by the sensors 16. A television 14 has a second transceiver 22 for receiving the information collected by the sensors 16, the television 14 has a processing unit 24 operationally coupled to the second transceiver 22 such that the processing unit 24 processes information received by the second transceiver 22. The television 14 is for displaying the information on a screen of the television 14.

The remote control 12 has a plurality of television control buttons 26 located on an upper surface 28 of the remote control 12. The plurality of television control buttons 26 is for controlling the television 14. The remote control 12 has a plurality of vital sign buttons 30 each is operationally coupled between at least one of the sensors 16 and the first transceiver 18 such that actuation of each of the vital sign buttons 30 transmits vital sign information to the television 14.

The plurality of sensors 16 is positioned on a pair of side surfaces 32 and a bottom surface 34 such that each of the sensors 16 is designed for contacting surfaces of a hand of the user when the remote control 12 is held in the hand of a user. A call button 36 is operationally coupled to the remote control 12, the call button 36 is for actuating an autodialer 38, and the autodialer 38 is designed for contacting emergency personnel upon depression of the call button 36.

The television 14 has a screen 40 for displaying the vital signs information collected by the sensors 16 when a user holds the remote control 12. The television has a medication reminder assembly 42 that is designed for reminding the user of a time to take medication. The medication reminder assembly 42 includes a timing unit 44 that is operationally coupled to the processing unit 24 such that the timing unit 44 is designed for timing intervals between when the user is to take medication.

An alert assembly 46 is positioned on the remote control 12 such that the alert assembly 46 is operationally coupled to the first transceiver 18 such that the alert assembly 46 is designed for signaling the user when to take medication. At least one of the sensors 16 is designed for monitoring a heart rate of the user and at least one of the sensors 16 is designed for monitoring a body temperature of the user.

In use, a user would hold the remote control in their hand and it wold take the vital signs of the user and transmit them to the television to be displayed on the screen. If there was a medical emergency a user depress the call button to activate a call through the autodialer to an emergency medical unit.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A vital sign monitoring system for monitoring the vital signs of a user, the vital sign monitoring system comprising:
   a remote control for television having a plurality of sensors, adapted for monitoring the vital signs of a user;
   a first transceiver being positioned in said housing such that said transceiver is operationally coupled to said sensors whereby said first transceiver is for transmitting vital sign information collected by said sensors; and
   a television having a second transceiver for receiving said information collected by said sensors, said television having a processing unit operationally coupled to said second transceiver such that said processing unit processes information received by said second transceiver, said television for displaying said information on a screen of said television;
   wherein said television has a medication reminder assembly being adapted for reminding the user of a time to take medication, said medication reminder assembly comprising a timing unit operationally coupled to said processing unit such that said timing unit is adapted for timing intervals between when the user is to take medication.

2. The vital signs monitoring system of claim 1, wherein said remote control has a plurality of television control buttons located on an upper surface of said remote control, said plurality of television control buttons for controlling said television.

3. The vital signs monitoring system of claim 1, wherein said remote control has a plurality of vital sign buttons each being operationally coupled between at least one of said sensors and said first transceiver such that actuation of each of said vital sign buttons transmits vital sign information to said television.

4. The vital signs monitoring system of claim 1, wherein said plurality of sensors are positioned on a pair of side surfaces and a bottom surface such that each of said sensors is adapted for contacting surfaces of a hand of the user when said remote control is being held in the hand of a user.

5. The vital signs monitoring system of claim 1, further comprises:
   a call button being operationally coupled to said remote control, said call button for actuating an autodialer, said autodialer being adapted for contacting emergency personnel upon depression of said call button.

6. The vital signs monitoring system of claim 1, wherein said television has a screen for displaying said vital signs information collected by said sensors when said remote control is held by a user.

7. The vital signs monitoring system of claim 1, further comprising:
   an alert assembly positioned on said remote control such that said alert assembly is operationally coupled to said first transceiver such that said alert assembly is adapted for signaling the user when to take medication.

8. The vital signs monitoring system of claim 1, wherein at least one of said sensors is adapted for monitoring a heart rate of the user.

9. The vital signs monitoring system of claim 1, wherein at least one of said sensors is adapted for monitoring a body temperature of the user.

10. A vital sign monitoring system for monitoring the vital signs of a user, the vital sign monitoring system comprising:
   a remote control for a television having a plurality of sensors adapted for monitoring the vital signs of a user;
   a first transceiver being positioned in said housing such that said transceiver is operationally coupled to said sensors whereby said first transceiver is for transmitting vital sign information collected by said sensors;
   a television having a second transceiver for receiving said information collected by said sensors, said television having a processing unit operationally coupled to said second transceiver such that said processing unit processes information received by said second transceiver, said television for displaying said information on a screen of said television;
   said remote control having a plurality of television control buttons located on an upper surface of said remote control, said plurality of television control buttons being for controlling said television;
   said remote control having a plurality of vital sign buttons each being operationally coupled between at least one of said sensors and said first transceiver such that actuation of each of said vital sign buttons transmits vital sign information to said television;
   said plurality of sensors positioned on a pair of side surfaces and a bottom surface such that each of said sensors is adapted for contacting surfaces of a hand of the user when said remote control is being held in the hand of a user;
   a call button being operationally coupled to said remote control, said call button being for actuating an autodialer, said autodialer being adapted for contacting emergency personnel upon depression of said call button;
   said television having a screen for displaying said vital signs information collected by said sensors when said remote control is held by a user;
   said television having a medication reminder assembly being adapted for reminding the user of a time to take medication, said medication reminder assembly comprising a timing unit operationally coupled to said processing unit such that said timing unit is adapted for timing intervals between when the user is to take medication;
   an alert assembly positioned on said remote control such that said alert assembly is operationally coupled to said first transceiver such that said alert assembly is adapted for signaling the user when to take medication;
   at least one of said sensors being adapted for monitoring a heart rate of the user; and
   at least one of said sensors being adapted for monitoring a body temperature of the user.

* * * * *